(12) United States Patent
Yamada et al.

(10) Patent No.: US 6,669,878 B2
(45) Date of Patent: Dec. 30, 2003

(54) METHOD OF MAKING A WATER DISINTEGRATABLE NON-WOVEN FABRIC

(75) Inventors: Daisuke Yamada, Kagawa (JP); Naohito Takeuchi, Kagawa (JP); Takayoshi Konishi, Kagawa (JP)

(73) Assignee: Uni-Charm Corporation, Kawanoe (JP)

(*) Notice: Subject to any disclaimer, the term of this patent is extended or adjusted under 35 U.S.C. 154(b) by 213 days.

(21) Appl. No.: 09/788,157

(22) Filed: Feb. 16, 2001

(65) Prior Publication Data

US 2001/0023160 A1 Sep. 20, 2001

Related U.S. Application Data

(62) Division of application No. 09/229,375, filed on Jan. 12, 1999, now Pat. No. 6,451,718.

(30) Foreign Application Priority Data

Jan. 16, 1998 (JP) .............................................. 98-6881

(51) Int. Cl.⁷ ................................................. D04H 1/64
(52) U.S. Cl. .......................... 264/103; 28/104; 264/129; 264/211.12; 264/211.14
(58) Field of Search ................................ 264/103, 129, 264/211.12, 211.14; 28/104

(56) References Cited

U.S. PATENT DOCUMENTS

| | | | | |
|---|---|---|---|---|
| 3,561,447 A | * | 2/1971 | Alexander | .................. 604/364 |
| 3,950,578 A | * | 4/1976 | Laumann | ..................... 427/378 |
| 4,959,894 A | * | 10/1990 | Jeffers et al. | |
| 5,281,306 A | | 1/1994 | Kakiuchi et al. | |

FOREIGN PATENT DOCUMENTS

| | | |
|---|---|---|
| EP | 0411752 A1 * | 2/1991 |
| JP | 07-24636 B2 | 3/1995 |
| JP | 09-228214 A | 9/1997 |
| WO | WO 98/44181 A1 * | 10/1998 |

* cited by examiner

Primary Examiner—Leo B. Tentoni
(74) Attorney, Agent, or Firm—Darby & Darby

(57) ABSTRACT

A water disintegratable non-woven fabric having excellent water disintegratability and high wet strength can be obtained by a step of forming a fiber web from fibers having a fiber length of 10 mm or less, a step of applying a water jet treatment to the fiber web to obtain a fiber sheet having wet strength of less than 100 g/25 mm in MD and CD, the wet strength being defined by tensile strength at break of the fiber sheet, as measured by using a tensilon tester with a chuck distance of 100 mm, at a tensile speed of 100 mm/min to the fiber sheet which is cut into 25 mm width and 150 mm length and impregnated with water in an amount 2.5 times the weight of the fiber sheet, and a step of adding at least one binder selected from the group consisting of carboxymethyl cellulose, alkylcellulose, polyvinyl alcohol and modified polyvinyl alcohol to the fiber sheet. The water disintegratable non-woven fabric is sufficiently bulky and has an excellent wiping effect.

11 Claims, 3 Drawing Sheets

(A)

(B)

METHOD OF MAKING A WATER DISINTEGRATABLE NON-WOVEN FABRIC

RELATED APPLICATIONS

The present application is a division of, U.S. patent application Ser. No. 09/229,375 filed on Jan. 12, 1999, now U.S. Pat. No. 6,451,718, having the same title as the present invention, which is hereby incorporated herein by reference in its entirety.

BACKGROUND OF THE INVENTION

1. Field of the Invention

The present invention relates to a method of manufacturing a water disintegratable non-woven fabric easily dispersed by water streams and the water disintegratable non-woven fabric obtained by the method. More specifically, it relates to a method of manufacturing a bulky water disintegratable non-woven fabric having excellent water disintegratability and wet strength and to the water disintegratable non-woven fabric obtained by the method.

2. Description of Related Art

Cleaning sheets made of paper or non-woven fabric are used for wiping human skins such as of hips or for cleaning toilet articles. The cleaning sheets are preferably water disintegratable so that they can be thrown away to toilets after use. Because, when they are thrown away into a toilet, it would take much time to disperse them in a septic tank unless they are highly water disintegratable, and they possibly clog drainages of the toilets.

Disposable fibrous cleaning sheets to be used for wiping are usually marketed while being packaged in a state previously wetted with liquid cleaning medicals in view of convenience and handlability. Such cleaning sheets must have wet strength sufficient to endure wiping in a state impregnated with liquid cleaning medicals, and are required to be water disintegratable when thrown away to toilets.

As such cleaning sheets, Japanese Patent Publication Hei 7-24636, for example, discloses a water disintegratable cleaning article containing a water soluble binder having carboxyl groups, metal ions and an organic solvent. The cleaning article has predetermined strength upon use, and when it thrown away into toilets, it tends to be dispersed in water since the binder is dissolved. However, since the cleaning article has, generally speaking, a constitution of paper, the fiber density is high. Accordingly, it can not give a bulky or soft feeling.

On the other hand, Japanese Patent Unexamined Publication Hei 9-228214 discloses a water disintegratable non-woven fabric obtained by mixing fibers having a fiber length of from 4 to 20 mm and pulp and entangling them by a high pressure water jet stream treatment and having wet strength of from 100 to 800 gf/25 mm as measured according to JIS P 8135. Since this non-woven fabric is formed by entangling fibers, it has a bulky feeling. However, this non-woven fabric is formed by entangling fibers having a long fiber length by a high pressure water jet treatment to provide relatively high wet strength. Therefore it is difficult to attain bulkiness, strength and water disintegratability in good balance, so that this non-woven fabric is not suitable to be thrown away into flushing toilets.

SUMMARY OF THE INVENTION

An object of the present invention is to provide a water disintegratable non-woven fabric having satisfactory water disintegratability and high wet strength, as well as having a bulky and soft feeling.

Another object of the present invention is to provide a water disintegratable non-woven fabric having an excellent wiping effect.

The objects and advantages of the present invention are attainable by a method of manufacturing a water disintegratable non-woven fabric comprising:

- a step of forming a fiber web from fibers having a fiber length of 10 mm or less,
- a step of applying a water jet treatment to the fiber web to obtain a fiber sheet having wet strength of less than 100 g/25 mm in MD and CD, the wet strength being defined by tensile strength at break of the fiber sheet, as measured by using a tensilon tester with a chuck distance of 100 mm, at a tensile speed of 100 mm/min to the fiber sheet which is cut into 25 mm width and 150 mm length and impregnated with water in an amount 2.5 times the weight of the fiber sheet, and
- a step of adding at least one binder selected from the group consisting of carboxymethyl cellulose, alkylcellulose, polyvinyl alcohol and modified polyvinyl alcohol to the fiber sheet, to obtain a water disintegratable non-woven fabric.

The present invention further provides a water disintegratable non-woven fabric, obtained by the method.

In the present invention, the fiber sheet is obtained to have predetermined wet strength by applying the water jet treatment to the fiber web. Then, the binder is added to the fiber sheet to obtain a water disintegratable non-woven fabric where wet strength is further enhanced. This non-woven fabric has high wet strength upon wiping, and can be readily disintegrated in water when it is brought into contact with a large quantity of water, because the binder is dissolved or swollen to release the bonding between the fibers.

In addition, the water disintegratable non-woven fabric of the present invention has a bulky soft feeling and an excellent wiping effect.

The basis weight of the fiber web is preferably from 20 to 100 g/m$^2$.

The fiber preferably comprises pulp of conifer and rayon having a fiber length of 7 mm or less. In this case, preferably, the blending ratio of the pulp of conifer is 30% by weight or more and the blending ratio of the rayon is 70% by weight or less.

The fiber density of the fiber sheet is preferably 0.3 g/cm$^3$ or less.

It is preferred that the work load of the water jet treatment per one processing is from 0.05 to 0.5 kW/m$^2$ and the fiber web is processed with the water jet treatment from 2 to 4 times. In this case, the water jet treatment is preferably conducted by using nozzles having a diameter of from 90 to 100 μm and aligned each at an interval of from 0.3 to 0.7 mm in CD.

The water disintegratability of the fiber sheet is preferably 100 sec or less as measured by a toilet paper disintegratability test according to JIS P 4501.

The content of the binder is preferably from 0.5 to 30 g based on 100 g of the fibers.

An aqueous solution in which an electrolyte selected from the group consisting of water soluble organic and inorganic salts is dissolved are preferably impregnated in the non-woven fabric, after the step of adding the binder.

The water disintegratable non-woven fabric of the present invention preferably has water disintegratability of 120 sec or less as measured by a toilet paper disintegratable test according to JIS P 4501.

DETAILED DESCRIPTION OF THE PREFERRED EMBODIMENTS

Figure 1:
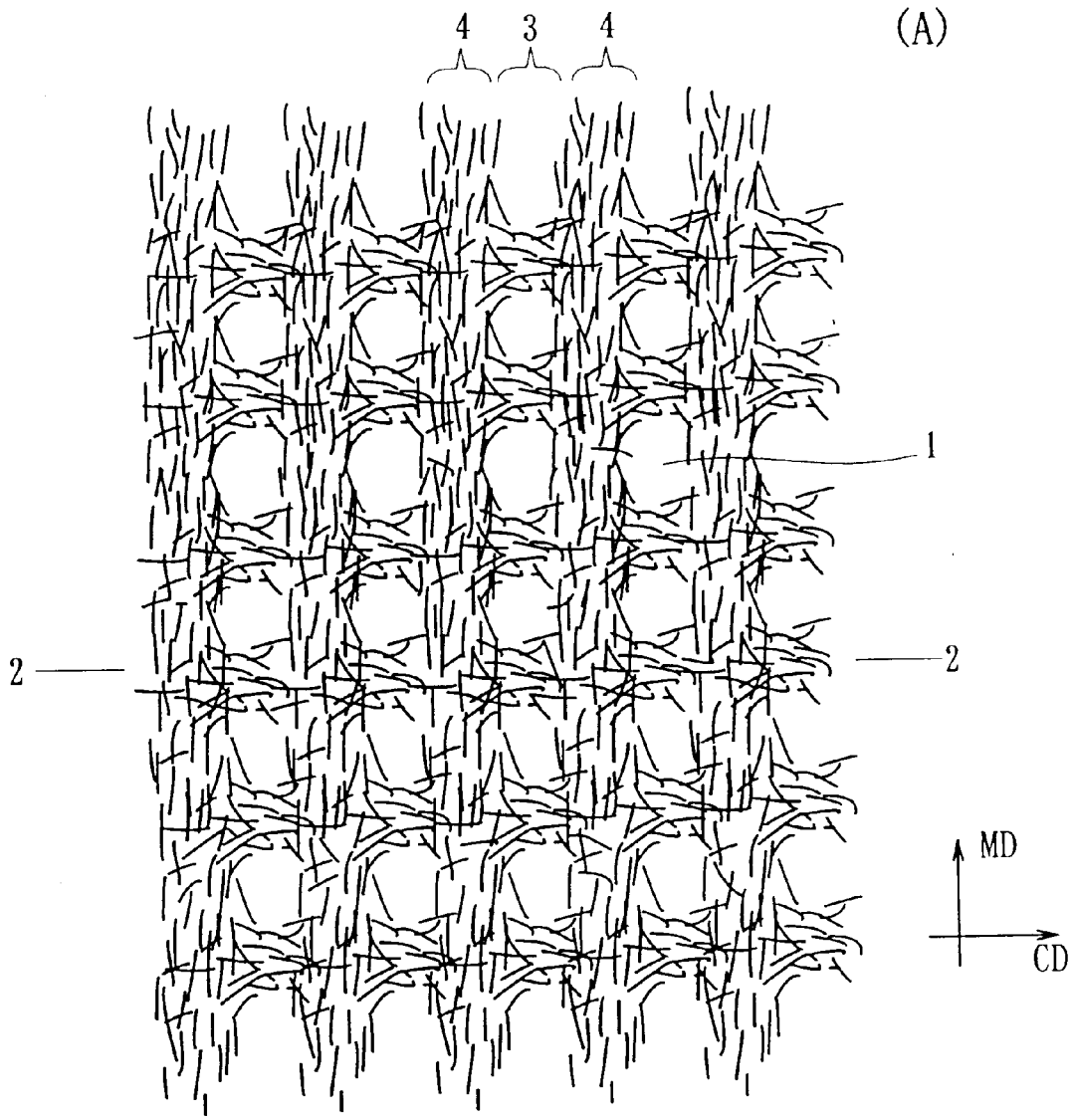
FIG. 1(A) is a partially enlarged plane view of a fiber sheet of the present invention and FIG. 1(B) is a cross sectional view taken along the line 2—2 of the FIG. 1(A)
Figure 1:
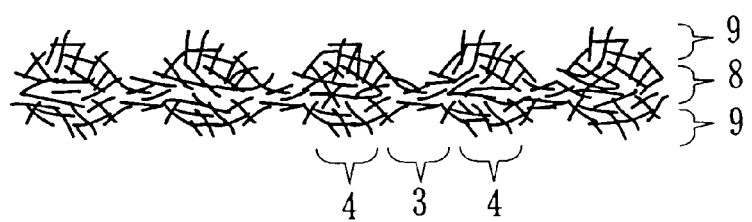

A water disintegratable non-woven fabric of the present invention is obtained by incorporating a binder to a fiber sheet which is formed by applying a water jet treatment to a fiber web. The fiber web is a mass of fibers in the form of a sheet in which the direction of the fibers is aligned to some extent.

In the present invention, the fibers constituting the fiber web are highly dispersible in water and have a fiber length of 10 mm or less. The dispersibility in water mentioned herein has the same meaning as the water disintegratability, and means the characteristic of fibers that they are disintegrated from each other upon contact with a large quantity of water. The fiber length in the present invention means an average fiber length.

In the present invention, either or both of chemical and natural fibers can be used. The chemical fibers can include, for example, rayon and acetate as regenerated fibers, polypropylene as synthetic fibers, and wooden pulp such as pulp of conifer and pulp of hardwood, Manila hemp, linter pulp, bamboo pulp, kenaf as natural fibers. In addition, the above-mentioned fibers, as a main ingredient, may be incorporated with natural fibers such as cotton, synthetic fibers such as polypropylene, polyvinyl alcohol, polyester, polyacrylonitrile and nylon, and synthetic pulp such as made of polyethylene, as well as inorganic fibers such as glass wool.

Among those fibers, natural fibers and rayon as regenerated fiber are especially preferred since they have high water dispersibility and water biodegradability.

Explanations will be made below mainly to rayon as an example of the fibers, but other fibers having the same characteristic and the same fiber length may of course be adopted instead of rayon.

A fiber length of the rayon to be used in the present invention is 10 mm or less. When rayon has a fiber length of from 10 to 7 mm, fibers of a shorter fiber length, for example, pulp of conifer is preferably blended together with the rayon, since the pulp of conifer has good water dispersibility. Because the pulp of conifer has an average fiber length as short as 1.0 to 4.5 mm, it acts like a disintegrating agent when the non-woven fabric is brought into contact with a large quantity of water, to make the non-woven fabric easily disintegratable. The pulp of conifer preferably has a degree of Canadian Standard Freeness (CSF: measured value according to JIS P 8121) of from 400 cc to 750 cc. If the CSF is smaller than 400 cc, namely, when pulp of conifer with excessive beating is used, the soft feeling (color and touch) of the non-woven fabric is deteriorated. More preferably, the CSF is from 500 cc to 750 cc. As the pulp of conifer, bleached kraft pulp of conifer is generally used preferably.

In this case, it is preferable that the blending ratio of the rayon is 70% by weight or less and the blending ratio of the pulp of conifer is 30% by weight or more, to the total weight of the fibers. If the blending ratio of the rayon is increased to 70% by weight or more, the water disintegratability of the non-woven fabric is deteriorated greatly.

It is further preferable that the fiber length of rayon is 7 mm or less. If the rayon having the fiber length of 7 mm or less is used, the water disintegratability of the non-woven fabric is further enhanced. In addition, if the fiber length of rayon is 7 mm or less, pulp of conifer may not be blended. However, even in this case, if the pulp of conifer is blended to the rayon at the blending ratio of 30% by weight or more to the total weight of the fibers, a water disintegratable non-woven fabric having water disintegratability and wet strength in good balance can be obtained.

There is no particular restriction for the lower limit of the fiber length. Fibers having further shorter fiber length can be adopted so long as they can form a fiber sheet during production steps.

The fineness of the rayon is preferably 0.5 denier or more when the fiber length of rayon is from 10 to 7 mm. If it is less than 0.5 denier, the extent of entanglement of the rayon by a water jet treatment is increased to deteriorate the water disintegratability of the non-woven fabric.

In the present invention, the basis weight of the fiber web is preferably from 20 to 100 g/m$^2$. If the basis weight is smaller than the lower limit, necessary strength can not be obtained. If the basis weight is greater than the upper limit, the resulting non-woven fabric lacks in the flexibility. In addition, the fibers constituting the non-woven fabric become less dispersible, so that the water disintegratability of the non-woven fabric is degraded. In addition, when the water disintegratable non-woven fabric of the present invention is used as a cleaning sheet, the further preferable basis weight of the fiber web is from 30 to 80 g/m$^2$ since the strength, wiping effect for stains and soft feeling are improved.

In the present invention, after forming the fiber web, for example, by a wet method, the fiber web is subjected to a water jet treatment to form the fiber sheet. A device of high pressure water jet streams ordinarily used is adopted for the water jet treatment.

Figure 2:
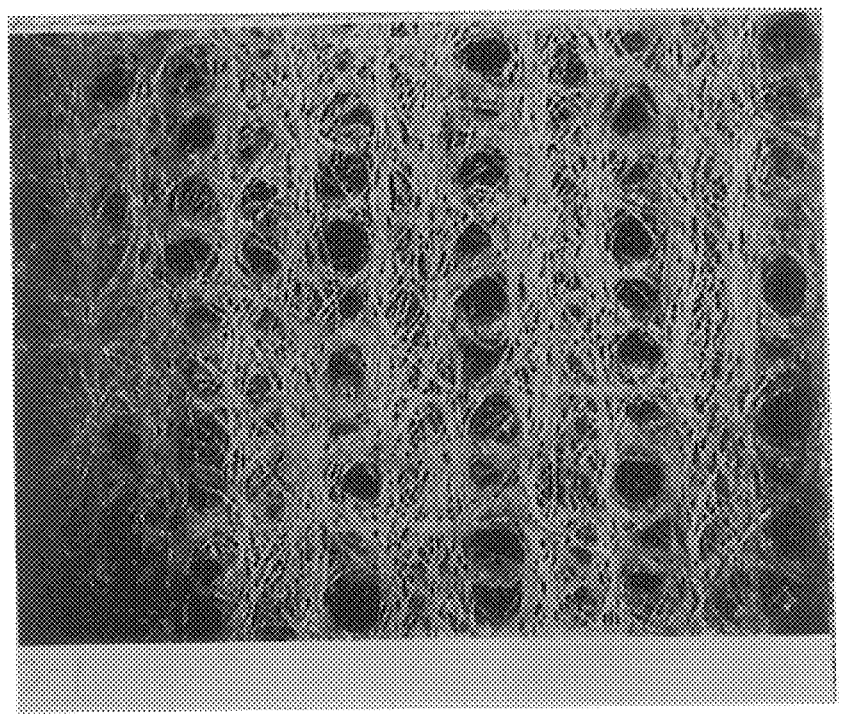
FIG. 2 is a microscopic photograph (20× magnification) for a partially enlarged plane view of the fiber sheet of the present invention.
Figure 3:
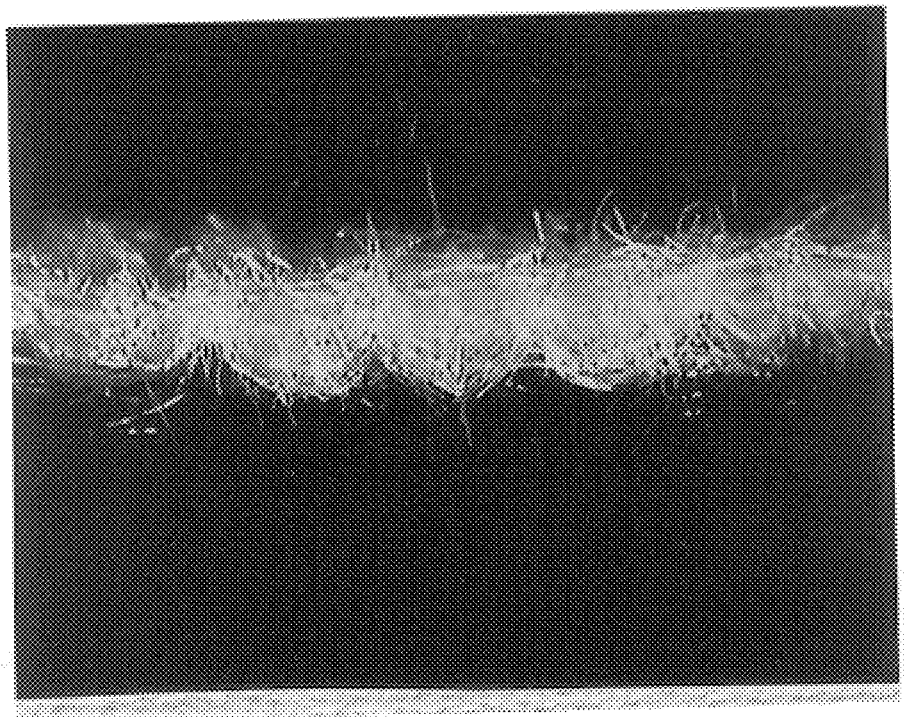
FIG. 3 is a microscopic photograph (20× magnification) for a partially enlarged cross sectional view of the fiber sheet of the present invention.

FIG. 1(A) is a partially enlarged plane view for the schematic structure of the fiber sheet after the water jet treatment and FIG. 2 is a microscopic photograph corresponding to FIG. 1(A). FIG. 1(B) is a cross sectional view taken along line 2—2 of FIG. 1(A) and FIG. 3 is a microscopic photograph corresponding to FIG. 1(B). In the water jet treatment, water jet streams are applied to the fiber web placed on a mesh by a high pressure water jet streams device. In this case, regions 1 from which the fibers are removed by water jet streams are formed at openings of the mesh. Further, regions 3 where fibers are less present and regions 4 where many fibers are gathered are formed along the MD. As shown in FIG. 1(B), the bulkiness of the fiber sheet is significantly increased at the regions 4 where many fibers are gathered, while kept low in the regions 3 where fibers are less present. In addition, a fiber density of the fiber sheet is higher at a central portion 8 than at portions 9, 9 on both sides of the central portion 8 in the direction of the thickness. Because the amount and the density of the fibers are thus changed partially by the water jet treatment as described above, a fiber sheet having high bulkiness as a whole and having a soft feeling approximate to that of fabrics can be provided.

Explanations will be made in details for the water jet treatment. The fiber web is fed by a continuously moving mesh conveyor belt, and high pressure water jet streams are jetted so as to pass from the surface to the rear face of the fiber web. In the water jet treatment, the characteristics of the resulting non-woven fabric vary depending on the basis weight of the fiber web, the diameter of jetting nozzles, the number of the jetting nozzles and feeding speed of the fiber web (processing speed) when treating the fiber web. In the present invention, the work load of the water jet treatment per one processing, calculated by the following formula, is preferably from 0.05 to 0.5 kW/m$^2$, and the fiber web is preferably processed with the water jet treatment from 1 to 6 times, more preferably, from 2 to 4 times:

Work load (kW/m$^2$)=[1.63×jetting pressure (kg/cm)× jetting flow rate (m$^3$/min)]÷processing speed (m/min).

If the work load of the water jet treatment per one processing is greater than the upper limit, there may be a possibility that the fibers are entangled excessively to deteriorate the water disintegratability, or the fiber web is broken. On the contrary, if the work load of the water jet treatment per one processing is less than the lower limit, the bulkiness is deteriorated. The water jet treatment can be applied to one or both surfaces of the fiber web.

Figure 4:
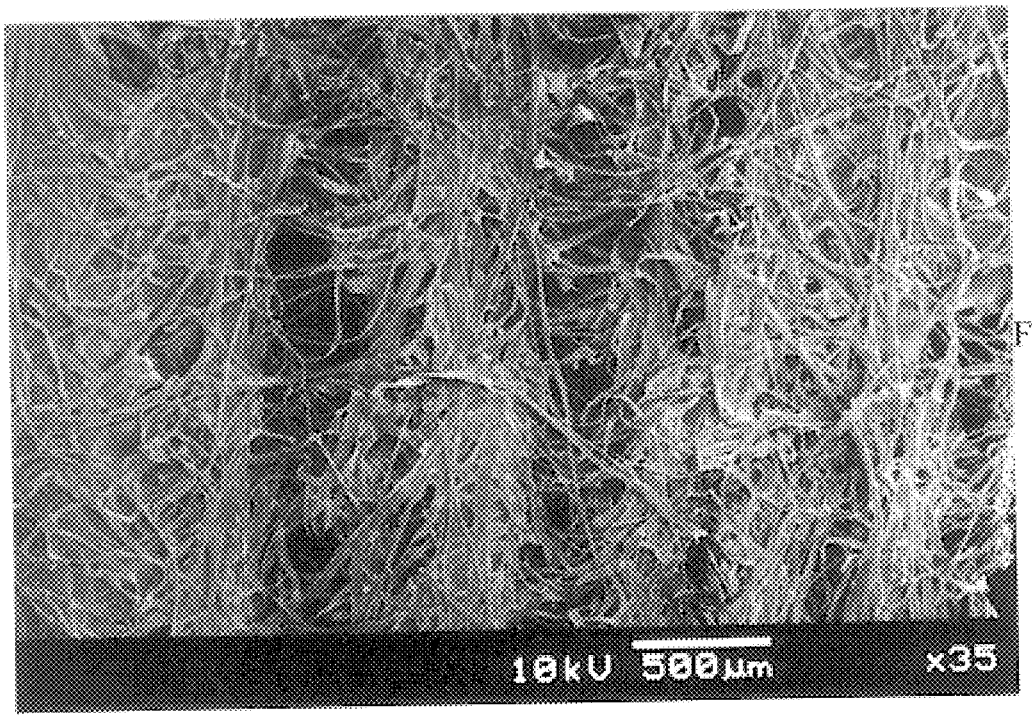
FIG. 4 is an electronic microscopic photograph (35× magnification) for a partially enlarged plane view of the fiber sheet of the present invention.

When the work load of the water jet treatment is within the range, it is further preferred that the jetting nozzles have a diameter of from 90 to 100 μm and are aligned each at an interval of from 0.3 to 0.7 mm in the CD direction. In this case, the entanglement of the fibers is appropriate so that the deterioration of the water disintegratability due to excessive entanglement and the deterioration of the wet strength due to insufficient entanglement can be prevented. By the way, since the fiber length of the fibers in the present invention is 10 mm or less, for example, about 7 mm, the extent of entanglement of the fibers with each other by the water jet treatment is lower than that of ordinary spun lace non-woven fabrics, as understood from FIG. 4.

After forming the fiber web, it is preferable in view of the convenience of the processing step that the fiber web is subjected to the water jet treatment without being dried. However, it is also possible to apply the water jet treatment after the fiber web is once dried.

The fiber sheet obtained by the steps described above has a strength at break of less than 100 g/25 mm in a wet state incorporated with water, in both of longitudinal direction (MD:Machine Direction) and lateral direction (CD:Cross direction) of the fiber sheet. The strength at break of the fiber sheet when wetted (hereinafter referred to as "wet strength") is a value when the fiber sheet does not contain a binder. The wet strength is a tensile strength (gf) at break when the fiber sheet cut into 25 mm width and 150 mm length and impregnated with water 2.5 times the weight of the fiber sheet is subjected to a measurement using a tensilon tester with a chuck distance of 100 mm and at a tensile speed of 100 mm/min. However, this is just an example of value given by the measuring method, and any fiber sheet having substantially the same strength as the wet strength described above may be adopted.

The fiber sheet obtained by the above-mentioned steps preferably has water disintegratability of 100 sec or less. The water disintegratability in this case is also a value measured in a state the fiber sheet does not contain a binder. The water disintegratability in this case is measured by the toilet paper disintegratability test according to JIS P 4501. An outline of the test for disintegratability is such that the fiber sheet as an object for the measurement is cut into 10 cm×10 cm in the longitudinal and lateral directions, charged into a 300 ml volume beaker containing 300 ml of ion exchange water and stirred by a rotor. The number of rotation is 600 rpm. The dispersed state of the fiber sheet is visually observed with lapse of time, and the time required for finely dispersing the fiber sheet is measured. However, it is just an example of a value given by the measuring method, and any fiber sheet having substantially the same water disintegratability described above may be adopted. In addition, fiber sheets having water disintegratability exceeding 100 sec but within about 120 sec may also be adopted depending on the application uses.

Furthermore, the fiber density of the fiber sheet obtained by the steps described above is preferably from 0.05/cm$^3$ to 0.3 g/cm$^3$.

The fiber sheet as described above is then incorporated with a binder, thereby increasing the wet strength, to obtain a water disintegratable non-woven fabric of the present invention.

The binder can include at least one compound selected from the group consisting of carboxymethyl cellulose, alkyl cellulose, polyvinyl alcohol and modified polyvinyl alcohol.

The carboxymethyl cellulose herein used is water soluble or water swellable. The alkylcellulose is a compound in which hydroxyl groups in an glucose ring unit of cellulose are substituted with alkyl groups. The alkylcellulose can includes, for example, methylcellulose, ethylcellulose and benzylcellulose. Among them, methylcellulose is especially preferred in view of satisfactory water disintegratability and wet strength. The modified polyvinyl alcohol is a vinyl alcohol type polymer containing a predetermined amount of sulphonic acid groups or carboxyl groups.

Since these binders are water soluble or water swellable, they are dissolved in water or swollen when brought into contact with a large quantity of water, so that the binders can be released from the fiber sheet. In this case, since the fiber sheet constituting the non-woven fabric has excellent water disintegratability, the non-woven fabric is disintegrated in water in a short period of time due to the release of the binder.

It is preferred that the binder is added to the fiber sheet by coating, for example, by using a silk screen.

Incidentally, when the binder is water swellable one, such as water swellable carboxymethyl cellulose described above, the binder may be added to the fiber sheet by mixing it to the fibers upon manufacturing the fiber web, thereby increasing the wet strength of the resulting non-woven fabric.

The adding amount of the binder is preferably from 0.5 to 30 g based on 100 g of the weight of the fibers. If the adding amount is less than the lower limit, the wet strength of the non-woven fabric is lowered. On the other hand, if the adding amount is more than the upper limit, the non-woven fabric is hardened to lower the soft feeling and, further also deteriorate water disintegratability.

The wet strength of the non-woven fabric thus produced (the fiber sheet added only with the binder) is preferably 250 g/25 mm or more both in MD and CD so as to be endurable to wiping. However, even if the wet strength of the non-woven fabric (the fiber sheet added only with the binder) is less than the lower limit, the wet strength of the resulting water disintegratable non-woven fabric can be improved by further incorporating electrolytes into the non-woven fabric.

The electrolytes can include either or both of organic and inorganic salts. The inorganic salts can include, for example, sodium sulfate, potassium sulfate, zinc sulfate, zinc nitrate, potassium alum, sodium chloride, aluminum sulfate, magnesium sulfate, potassium chloride, sodium carbonate, sodium hydrogen carbonate and ammonium carbonate. Organic salts can include, for example, sodium pyrrolidone carboxylate, sodium citrate, potassium citrate, sodium tartrate, potassium tartrate, sodium lactate, sodium succinate, calcium pantothenate, calcium lactate and sodium lauryl sulfate. When the carboxymethyl cellulose is used as the binder, bivalent salts are preferred as the electrolyte, since they increase the wet strength of the water disintegratable non-woven fabric. When the alkyl cellulose is used as the binder, monovalent salts are preferable as the electrolyte. In addition, when the polyvinyl alcohol or the modified polyvinyl alcohol is used as the binder, monovalent salts are preferably used as the electrolyte.

In order to incorporate the electrolyte in the water disintegratable non-woven fabric, it is a convenient step to dissolve the electrolyte in water to obtain an aqueous solution, and impregnate the aqueous solution in the non-woven fabric. Accordingly, the electrolyte is preferably water soluble. In this case, it is preferable that the concentration of the electrolyte in the aqueous solution is from 0.5 to 10% by weight, more preferably, from 1.0 to 5.0% by weight, and 100 g of the water disintegratable non-woven fabric is impregnated with from 200 to 250 g of the aqueous solution thus prepared. As the content of the electrolyte is increased, the wet strength of the water disintegratable non-woven fabric is increased. However, in a case of using sodium sulfate as the electrolyte and using the water disintegratable non-woven fabric relative to human skins, the content of sodium sulfate is preferably reduced in order not to be stimulative to skins. A method of impregnating the aqueous solution in the water disintegratable non-woven fabric can include immersion and spraying.

In a case of using the alkylcelluloses as the binder, the following compounds can be further incorporated in order to enhance the wet strength of the water disintegratable non-woven fabric. For example, there can be mentioned copolymers of polymerizable acid anhydrides with other compounds such as (meth)acrylic acid-maleic acid type resin or (meth)acrylic acid-fumaric acid type resin. The copolymers are preferably saponified by reaction with sodium hydroxide to be partially formed into a water soluble sodium salt of carboxylic acid. In addition, further incorporation of an amino acid derivative such as trimthylglycine is also preferable in view of the wet strength.

As has been described above, a water disintegratable non-woven fabric having the wet strength (in MD and CD) of 250 g/25 mm or more can be obtained. This water disintegratable non-woven fabric has sufficient wet strength to be endurable to wiping, such as cleaning of a body, for example, hips of a baby and cleaning in a house, even in a state where it contains water to some extent, for example, from 2 to 2.5 times the weight of the nonwoven fabric.

The water disintegratability of the finally obtained water disintegratable non-woven fabric is preferably 120 sec or less as measured according to JIS P 4501. If it is less than 120 sec, the non-woven fabric can be thrown away in flush toilets with no problem. Further preferably, the water disintegratability of the finally obtained water disintegratable non-woven fabric is 100 sec or less.

As described above, since the portions 9 where the fiber density is reduced are formed near the surfaces of the water disintegratable non-woven fabric of the present invention, the portions 9 have an effect of keeping stains upon wiping. In addition, since the water disintegratable non-woven fabric of the present invention has unevenness on the surfaces by the water jet treatment, stains can be scraped off by the unevenness. Accordingly, the water disintegratable non-woven fabric of the present invention has a high wiping effect relative to both wet stains and dry stains.

In addition, the water disintegratable non-woven fabric of the present invention is bulky and has a thickness sufficient to provide good touch, so that wiping can be conducted easily. It further enhances the wiping effect. The thickness of the non-woven fabric is preferably 0.2 mm or more.

Furthermore, the water disintegratable non-woven fabric of the present invention may be incorporated with an organic solvent having an effect of removing stains and an effect of a humectant. Among organic solvents, a polyhydric alcohol such as glycerine is preferred, since it can enhance the wet strength of the water disintegratable non-woven fabric. Additionally, other materials can be incorporated in the water disintegratable non-woven fabric of the present invention so long as they do not inhibit the effect of the present invention. For example, surfactants, antibacterial agents, preservatives, deodorants, humectants and alcohols may be preferably incorporated. The water disintegratable non-woven fabric is neither deteriorated in the wet strength nor collapsed by such materials contained therein.

The water disintegratable non-woven fabric of the present invention can be stored in a state incorporated with water. The water disintegratability and the wet strength are hardly deteriorated even after long period of storage.

As described above, the water disintegratable non-woven fabric of the present invention can be used as wet tissues for human skins, as cleaning sheets for toilet articles and as any products of the kind to be discarded and thrown away in water. When packaging the water disintegratable non-woven fabrics of the present invention as a product previously wetted, it is marketed being sealed so as to prevent the non-woven fabrics from drying.

Alternatively, the water disintegratable non-woven fabric of the present invention can be marketed in a dried state. In this case, for example, the non-woven fabric, which is dried after addition of the binder, may be impregnated with water or an aqueous solution having the electrolyte dissolved therein upon use. Alternatively, the non-woven fabric, which is dried after addition of the binder and impregnation of an aqueous solution having the electrolyte dissolved therein, may be impregnated with water or liquid chemicals upon use.

The present invention will be explained more specifically by way of examples.

EXAMPLE A

Measurements were conducted for a fiber sheet in a state before application of a binder, which is a base of the water disintegratable non-woven fabric of the present invention.

Rayon fibers (manufactured by Toho Rayon Co. Ltd.) having a fiber length as shown in Table 1 and a fineness of 1.5 denier as a starting fiber were prepared in 0.2% concentration in water, and subjected to paper making on a plastic wire by a hand paper making machine in a laboratory to form a fiber web sized 25 cm×25 cm and having a basis weight of 40 g/m$^2$. The fiber web was placed on a transfer conveyor in a state being accumulated on the plastic wire without drying, and subjected to a water jet treatment while moving the fiber web at a speed of 30 m/min to entangle the fibers with each other. The high pressure water jet stream jetting device used in this case had 2000 nozzle holes each of a diameter of 95 μm arranged each at an interval of 0.5 mm per 1 m, and jetting was conducted at hydraulic pressure 30 kg/cm$^2$ so as to pass through from the surface to the rear face of the fiber web. The processing speed was 30 m/min. Then, second jetting was conducted again in the same manner. The work load of the water jet treatment was 0.18793 kW/m$^3$ per one processing. Subsequently, it was dried by using a hot blow drier to obtain a fiber sheet. 250 g of ion exchanged water was impregnated into 100 g of the fiber sheet. Measurements for the water disintegratability and the wet strength of the fiber sheets were conducted according to the method described below.

The measurement for the water disintegratability was conducted by the toilet paper disintegratability test according to JIS P 4501. Referring more specifically, a specimen prepared by cutting the fiber sheet into 10 cm length and 10 cm width was charged in a 300 mm volume beaker containing 300 ml of ion exchanged water, and stirred by using a rotor. The number of rotation was 600 rpm. The dispersed state of the fiber sheet was observed with lapse of time, and a time required for dispersion was measured (shown in tables: on the basis of second).

The wet strength was measured by using a specimen prepared by cutting the fiber sheet into 25 mm width and 150 mm length and using a tensilon tester with a chuck distance of 100 mm and at a tensile speed of 100 mm/min. Measurement was conducted in the machine direction (MD) and the cross direction (CD) of the fiber sheet, respectively. The strength at break (gf) upon measurement was determined as the result of the wet strength test (shown in tables: on the basis of g/25 mm).

Results are shown in Table 1.

TABLE 1

|  | Unit | Example 1 | Example 2 | Example 3 | Example 4 |
|---|---|---|---|---|---|
| Basis weight | g/m$^2$ | 40 | 40 | 40 | 41 |
| Thickness | mm | 0.43 | 0.42 | 0.39 | 0.57 |
| Density | g/m$^3$ | 0.09 | 0.10 | 0.10 | 0.07 |
| Wet strength MD | g/25 mm | 51 | 51 | 47 | 67 |
| CD | g/25 mm | 39 | 40 | 38 | 56 |
| Water disintegratability | sec | 110 | 62 | 41 | 89 |
| Denier of rayon | Denier | 1.5 | 1.5 | 1.5 | 1.5 |
| Fiber length of rayon | mm | 10 | 7 | 5 | 7 |
| Pressure of water jet | kg/cm$^2$ | 50 | 50 | 50 | 50 |
| Processing cycle of water jet | Cycle | 2 | 2 | 2 | 2 |

EXAMPLE B

Tests were conducted in the same manner for the fiber sheet.

A fiber web sized 25 cm×25 cm and having a basis weight as shown in Table 2 was formed by using rayon fibers (manufactured by Toho Rayon Co. Ltd.) having a fiber length of 7 mm and a fineness of 1.5 denier as a starting fiber in the same manner as in Example A. Then, a fiber sheet was obtained and the water disintegratability and the wet strength were measured in the same manner as in Example A.

As comparative examples, fiber sheets each having a basis weight of 15 g/cm$^2$ and a basis weight of 100 g/cm$^2$ were prepared in the same manner as in Example and the water disintegratability and the wet strength were measured in the same manner as in Example.

The results are shown in Table 2.

TABLE 2

|  | Unit | Comp. Exam 1 | Comp. Exam. 2 | Example 1 | Example 2 | Example 3 |
|---|---|---|---|---|---|---|
| Basis weight | g/m$^2$ | 15 | 100 | 25 | 41 | 80 |
| Thickness | mm | 0.16 | 0.78 | 0.27 | 0.4 | 0.65 |
| Density | g/m$^3$ | 0.09 | 0.13 | 0.09 | 0.1 | 0.12 |
| Wet strength |  |  |  |  |  |  |
| MD | g/25 mm | 8 | 76 | 20 | 49 | 67 |
| CD | g/25 mm | 7 | 60 | 14 | 37 | 52 |
| Water disintegratability | sec | 19 | 157 | 28 | 62 | 89 |
| Denier of rayon | Denier | 1.5 | 1.5 | 1.5 | 1.5 | 1.5 |
| Fiber length of rayon | mm | 7 | 7 | 7 | 7 | 7 |
| Pressure of water jet | kg/cm$^2$ | 50 | 50 | 50 | 50 | 50 |
| Processing cycle of water jet | Cycle | 2 | 2 | 2 | 2 | 2 |

EXAMPLE C

Tests were conducted in the same manner for the fiber sheet.

A fiber web sized 25 cm×25 cm and having a basis weight of 40 g/m$^2$ was formed by using rayon fibers (manufactured by Toho Rayon Co. Ltd.) having a fiber length of 7 mm and a fineness of 1.5 denier as starting fibers in the same manner as in Example A. Then, a fiber sheet was obtained in the same manner as in Example A by applying a water jet treatment under the conditions shown in Table 3, and the water disintegratability and the wet strength were measured.

As comparative examples, the water disintegratability and the wet strength were measured in the same manner as in Example with respect to fiber sheets which were prepared by changing the conditions of the water jet treatment.

The results are shown in Table 3.

TABLE 3

|  | Unit | Comp. Exam. 1 | Comp. Exam. 2 | Comp. Exam. 3 | Example 1 | Example 2 |
|---|---|---|---|---|---|---|
| Basis weight | g/m$^2$ | 40 | 40 | 42 | 41 | 42 |
| Thickness | mm | 0.12 | 0.22 | 0.62 | 0.4 | 0.51 |
| Density | g/m$^3$ | 0.33 | 0.18 | 0.07 | 0.1 | 0.08 |
| Wet strength |  |  |  |  |  |  |
| MD | g/25 mm | 41 | 42 | 68 | 49 | 56 |
| CD | g/25 mm | 40 | 38 | 35 | 37 | 38 |
| Water disintegratability | sec | 10 | 15 | 189 | 62 | 91 |
| Denier of rayon | Denier | 1.5 | 1.5 | 1.5 | 1.5 | 1.5 |
| Fiber length of rayon | mm | 7 | 7 | 7 | 7 | 7 |
| Pressure of water jet | kg/cm$^2$ | 0 | 30 | 50 | 50 | 50 |
| Processing cycle of water jet | cycle | 0 | 1 | 8 | 2 | 4 |

EXAMPLE D

Fiber sheets were obtained in the same manner as in Example A by changing the blending ratio of bleached craft pulp of conifer (NBKP, Canadian Standard Freeness (CSF)= 740 ml) to rayon fibers by weight as shown in Table 4. As the rayon fibers, use is made of the rayon fibers having a fiber length of 5 mm used in Example A. An aqueous solution having methyl cellulose (manufactured by Shinetsu Chemical Co. Ltd.) dissolved therein in a 1 wt % concentration was prepared, and the methyl cellulose was coated on the fiber sheets by about 3 g/m² by spraying the aqueous solution thereto, and then the sheets were dried again by using a hot blow type drier to obtain a water disintegratable non-woven fabric. Thereafter, 100 g of the non-woven fabric was impregnated with 250 g of an aqueous solution comprising sodium sulfate, trimethyl glycine, propylene glycol and water at a weight ratio of 4.5:4.5:5:86. The same measurements for the water disintegratability and the wet strength as in Example A were conducted for the water disintegratable non-woven fabrics thus obtained.

As a comparative example, a non-woven fabric to which the water jet treatment was not applied was prepared in the same manner as in the Example, and measurements for the water disintegratability and the wet strength were conducted.

The results are shown in Table 4.

TABLE 4

| | | Unit | Comp Exam 1 | Example 1 | Example 2 |
|---|---|---|---|---|---|
| Blend of fiber | Rayon | % | 70 | 70 | 30 |
| | NBKP | % | 30 | 30 | 70 |
| Basis weight | | g/m² | 44 | 43 | 43 |
| Thickness | | mm | 0.13 | 0.40 | 0.32 |
| Density | | g/cm³ | 0.34 | 0.11 | 0.13 |
| Wet strength | MD | g/25 mm | 408 | 340 | 618 |
| | CD | g/25 mm | 395 | 312 | 566 |
| Water disintegratability | | sec | 9 | 22 | 24 |

EXAMPLE E

Water disintegratable non-woven fabrics were obtained in the same manner as in Example D except for changing the basis weight as shown in Table 5 (the blending ratio of bleached craft pulp of conifer to rayon fibers is 30:70 by weight and the aqueous solution to be impregnated with the non-woven fabrics was also the same as in Example D). Measurements was conducted for the water disintegratability and the wet strength in the same manner as in Example A for the water disintegratable non-woven fabric.

The results are shown in Table 5.

TABLE 5

| | Unit | Example 1 | Example 2 | Example 3 | Example 4 | Example 5 |
|---|---|---|---|---|---|---|
| Basis weight | g/m² | 15 | 20 | 40 | 80 | 100 |
| Thickness | mm | 0.22 | 0.27 | 0.40 | 0.71 | 0.94 |
| Density | g/cm³ | 0.07 | 0.07 | 0.10 | 0.11 | 0.11 |
| Wet strength | | | | | | |
| MD | g/25 mm | 204 | 255 | 340 | 550 | 683 |
| CD | g/25 mm | 168 | 208 | 312 | 506 | 630 |
| Water disintegratability | sec | 7 | 15 | 22 | 73 | 105 |

EXAMPLE F

Water disintegratable non-woven fabrics were obtained in the same manner as in Example D. 100 g of the water disintegratable non-woven fabric was impregnated with 250 g of liquid medical shown below by using a spray, instead of the aqueous solution in Example D. The liquid medical was composed of sodium sulfate anhydride; trimethylglycine; propylene glycol; partial sodium salt of (meth)acrylic acid (ester)-maleic acid copolymer and pure water at a weight ratio of 4.5: 4.5:5:1:85. The water disintegratable non-woven fabric impregnated with the liquid medical was stood still at 20° C. for 24 hours, and the water disintegratability and the wet strength were measured in the same manner as in Example A.

As a comparative example, a non-woven fabric formed in the same manner except for not applying the water jet treatment (the blending ratio of bleached craft pulp of conifer to rayon fibers is 30:70 by weight) was prepared. The water disintegratability and the wet strength were measured. Since the non-woven fabric in the comparative example was not subjected to water jetting, the thickness was insufficient, and was not suitable to wiping.

The results are shown in Table 6.

TABLE 6

| | | Unit | Comp Exam 1 | Example 1 | Example 2 |
|---|---|---|---|---|---|
| Blend of fiber | Rayon | % | 70 | 70 | 30 |
| | NBKP | % | 30 | 30 | 70 |
| Basis weight | | g/m² | 44 | 43 | 43 |
| Thickness | | mm | 0.13 | 0.41 | 0.32 |
| Density | | g/cm³ | 0.34 | 0.1 | 0.13 |
| Wet strength | MD | g/25 mm | 584 | 487 | 883 |
| | CD | g/25 mm | 565 | 446 | 809 |
| Water disintegratability | | sec | 9 | 21 | 22 |

A measurement for wiping effect was conducted by using the water disintegratable non-woven fabric in Example 1 shown in Table 6 as a cleaning sheet. The method is as follows.

Dry stains and wet stain were sprayed on a plastic plate of 30 cm×30 cm. 0.2 g of test dusts (7 kinds of test dusts according to JIS Z 8901) were used as the dry stains, and 0.5 ml of a sauce of medium concentration was used as the wet stain. A specimen of 20 cm×15 cm prepared by cutting the non-woven fabric in Example 1 shown in Table 6 was folded in two at the size of 10 cm×15 cm, and it was placed on the plastic plate. A small plastic plate of 10 cm×5 cm was placed on the folded specimen, and the stains on the plastic plate were wiped off at a moving speed of 5 m/min by using a force gage. Since a weight of 200 g was placed on the small plastic plate, the force exerted on the folded specimen upon moving was at a pressure of 0.5 kg. The operation of wiping the entire surface of the plastic plate is defined as one cycle, and the wiping was repeated till elimination of the stains on the plastic plate was completed, and the number of cycles of the wiping was recorded.

As comparative example 1, measurement was conducted in the same manner as in Example by using the non-woven fabric of the comparative example shown in Table 6.

In addition, in order to show that the wiping effect of the non-woven fabric depended on the bulkiness, a non-woven fabric, which was subjected to a hot pressing treatment after applying the water jet treatment, namely, before incorporating the binder, in the same production process as for the non-woven fabric of Example 1 shown in Table 6, was prepared, and the same measurement for wiping effect was conducted as comparative example 2. The hot pressing treatment was conducted for 30 sec under the conditions of a pressure of 20 kg/cm² and a temperature of 100° C., so that the non-woven fabric was pressed to have the same bulkiness (thickness) as before conducting the water jet treatment.

The results are shown in Table 7.

TABLE 7

|  |  | Comp. Exam. | Comp. Exam 2 | Example 1 |
|---|---|---|---|---|
| Water jet treatment |  | None | ◯ | ◯ |
| Hot press treatment |  | None | ◯ | None |
| Basis weight | g/m² | 44 | 43 | 43 |
| Thickness | mm | 0.13 | 0.13 | 0.41 |
| Density | g/cm³ | 0.34 | 0.33 | 0.10 |
| Dry stains | times | 4 | 4 | 2 |
| Wet stain | times | 3 | 3 | 2 |

As can be seen from Table 7, the number of cycles of wiping required for complete removal of stains is small in the Example 1. Namely, it can be seen that labors can be saved in the wiping operation by using the water disintegratable non-woven fabric of the present invention.

While in the foregoing specification this invention has been described in relation to preferred embodiments and many details have been set forth for purpose of illustration it will be apparent to those skilled in the art that the invention is susceptible to additional embodiments and that certain of the details described herein can be varied considerably without departing from the basic principles of the invention.

Further, 'comprises/comprising' when used in this specification is taken to specify the presence of stated features, integers, steps or components but dose not preclude the presence or addition of one or more other features, integers, steps, components or groups thereof.

What is claimed is:

1. A method of manufacturing a water disintegratable non-woven fabric, comprising:
   a step of forming a fiber web from fibers having a fiber length of 10 mm or less,
   a step of applying a water jet treatment to the fiber web to obtain a fiber sheet having a wet strength of less than 100 g/25 mm in MD and CD;
   a step of adding a binder of alkylcellulose to the fiber sheet, to obtain a water disintegratable non-woven fabric; and
   a step of impregnating the non-woven fabric with an aqueous solution in which an electrolyte selected from the group consisting of monovalent organic salt and monovalent inorganic salt is dissolved.

2. A method of manufacturing a water disintegratable non-woven fabric as defined in claim 1, wherein a basis weight of the fiber web is from 20 to 100 g/m².

3. A method of manufacturing a water disintegratable non-woven fabric as defined in claim 2, wherein the fibers comprise pulp of conifer and rayon having a fiber length of 7 mm or less.

4. A method of manufacturing a water disintegratable non-woven fabric as defined in claim 3, wherein a blending ratio of the pulp of conifer is 30% by weight or more, the blending ratio of the rayon is 70% by weight or less.

5. A method of manufacturing a water disintegratable non-woven fabric as defined in claim 2, wherein a work load of the water jet treatment per one processing is from 0.05 to 0.5 kW/m² and the fiber web is processed with the water jet treatment from 2 to 4 times.

6. A method of manufacturing a water disintegratable non-woven fabric as defined in claim 5, wherein the water jet treatment is conducted by using nozzles having a diameter of from 90 to 100 μm and aligned each at an interval of from 0.3 to 0.7 mm in CD.

7. A method of manufacturing a water disintegratable non-woven fabric as defined in claim 5, wherein water disintegratability of the fiber sheet is 100 sec or less.

8. A method of manufacturing a water disintegratable non-woven fabric as defined in claim 7, wherein a content of the binder is from 0.5 to 30 g based on 100 g of the fibers.

9. A method of manufacturing a water disintegratable non-woven fabric as defined in claim 2, wherein a content of the binder is from 0.5 to 30 g based on 100 g of the fibers.

10. A method of manufacturing a water disintegratable non-woven fabric as defined in claim 1, wherein the fiber sheet further comprises:

copolymers of polymerizable acid anhydride compounds; and amino acid derivatives.

11. A method of manufacturing a water disintegratable non-woven fabric as defined in claim 10, wherein the alkylcellulose is methylcellulose, the electrolyte is sodium sulfate, the copolymer is partial sodium salt of (meth)acrylic acid (ester)-maleic acid copolymer, and the amino acid derivative is trimethyl glycine.

* * * * *